United States Patent [19]
Barrett

[11] Patent Number: 5,370,690
[45] Date of Patent: Dec. 6, 1994

[54] ARTIFICIAL BLADDER

[75] Inventor: David M. Barrett, Rochester, Minn.

[73] Assignee: Mayo Foundation for Medical Education and Research, Rochester, Minn.

[21] Appl. No.: 843,669

[22] Filed: Feb. 28, 1992

[51] Int. Cl.$^5$ ............................ A61F 2/04; A61F 2/02
[52] U.S. Cl. ........................................ 623/12; 623/11; 600/30
[58] Field of Search .................................. 600/29–31; 623/11, 12; 604/4, 5

[56] References Cited

U.S. PATENT DOCUMENTS

| | | |
|---|---|---|
| 3,810,259 | 5/1974 | Summers . |
| 4,044,401 | 8/1977 | Guiset . |
| 4,167,952 | 9/1979 | Reinicke . |
| 4,222,377 | 9/1980 | Burton . |
| 4,961,747 | 10/1990 | Wascher et al. . |
| 4,969,474 | 11/1990 | Schwarz . |
| 4,976,735 | 12/1990 | Griffith et al. . |
| 5,012,822 | 5/1991 | Schwarz . |
| 5,019,102 | 5/1991 | Hoene . |
| 5,041,077 | 8/1991 | Kulick . |

OTHER PUBLICATIONS

B. Friedman, D. Smith, and A. Finkle, *Prosthetic Bladder of Silicone Rubber in Dogs*, Investigative Urology, vol. I, pp. 323-338 (1964).

L. Belden, G. Kushner, U. Wascher, M. Naslund, and J. Mostwin, *Design, Fabrication, Evaluation and Iterations of Tailored Urinary Bladder Prosthesis*, Journal of Urology, vol. 143 Suppl. 1, p. 410A (1990).

C. Abbou, J. Leandri, J. Auvert, and P. Rey, *New Prosthetic Bladder*, Trans-American Society for Artificial Internal Organs, vol. 23, pp. 271-374 (1977).

H. Melchior, P. Rathert, A. Schiffer, W. Lutzeyer, *Etude fonctionnelle de l'uretere apres remplacement partiel par prothese en elastomere de silicone*, Journal Urology and Nephrology (Paris), vol. 77, Suppl. 2, pp. 515-521 (1971). A copy of an English translation is attached thereto.

J. P. Bordat, *Etude experimentale d'une prothese vesicale en elastomere de silicone*, Journal Urology and Nephrology (Paris), vol. 82, Suppl. 2, pp. 498-505 (1976). A copy of an English translation is attached thereto.

A. Apoil, A. Granger, A. Sausse and A. Stern, *Experimental and Clinical Studies of Prosthetic Bladder Replacement*, Genitourinary Reconstruction with Prosthesis, pp. 75-80 (1981).

C. Abbou and J. Auvert, *Prosthetic Bladder Replacement in Dogs*, Genitourinary Reconstruction with Prosthesis, pp. 71-75 (1981).

E. Rigotti, D. Randone, A. Tizzani, B. Fren and M. Bargro, *Sostituzione Totale Della Bescica Con Protesi*, Minerva Urol, vol. 28, pp. 1-5 (1976). A copy of an English translation of this publication is attached thereto.

M. Donovan, *The Testing of Biocompatibility of Alouplastic Materials in Genitourinary Track Suitable for Use as Prosthetic Materials*, Thesis, University of Dublin, Trinity College, Dublin, Ireland (1984).

Primary Examiner—Jerome L. Kruter
Assistant Examiner—Elizabeth M. Burke
Attorney, Agent, or Firm—Merchant, Gould, Smith, Edell, Welter & Schmidt

[57] ABSTRACT

An apparatus for use as an artificial bladder for implantation into a patient. The apparatus is comprised of a bladder having a rigid outer shell and a flexible inner shell that are connected at a bladder neck thereby creating an open space between the outer shell and inner shell that contains a biocompatible fluid, a storage unit for storing the biocompatible fluid at a pressure lower than the pressure inside the bladder, a pumping unit for creating a positive pressure to pump the biocompatible fluid from the storage unit to the open space in the bladder, a ureter replacement unit for allowing urine to move from the kidneys to the inner shell of the bladder, a valve unit for allowing the urine to exit the bladder, a urethra replacement unit for allowing the urine to exit the body from the valve unit and tubine units for allowing the biocompatible fluid to move between the bladder, storage unit and pumping unit.

12 Claims, 3 Drawing Sheets

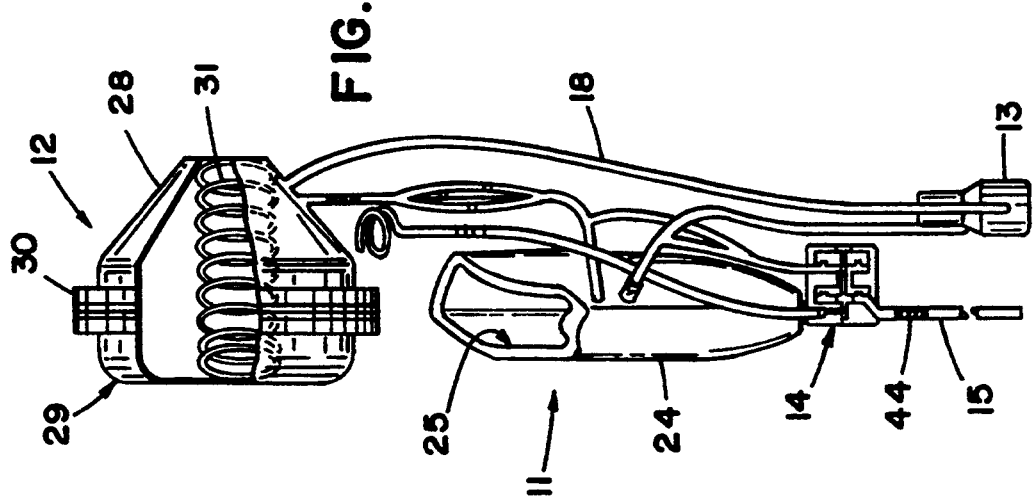
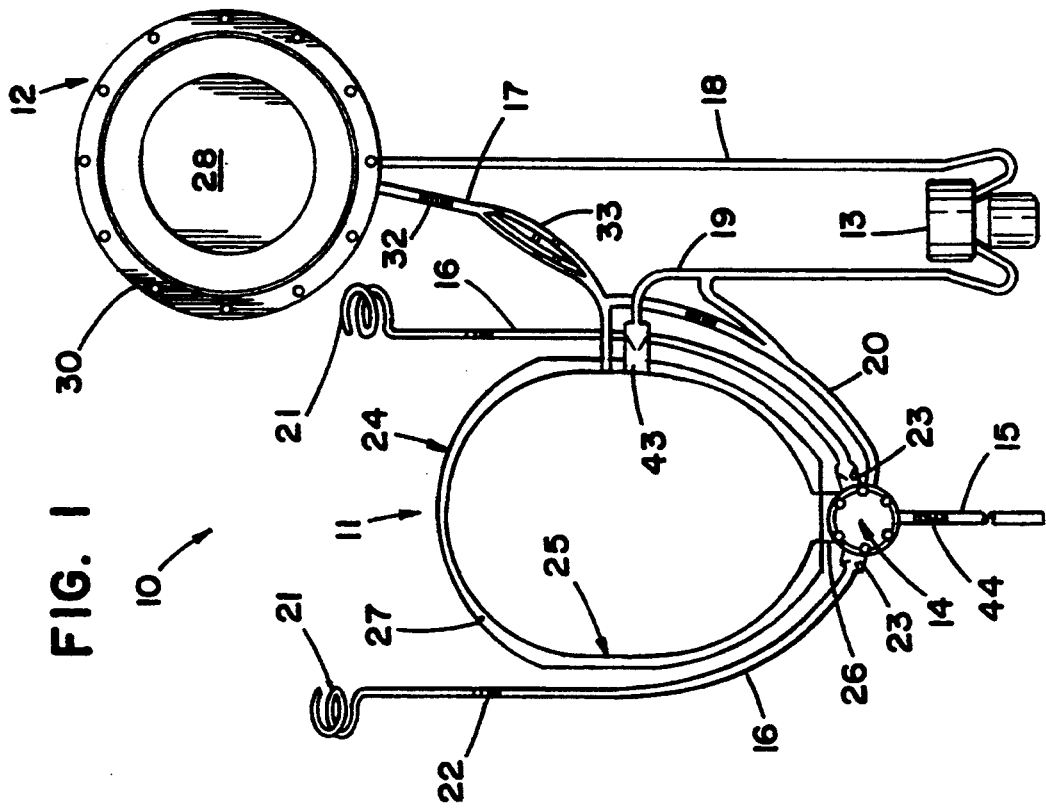

ARTIFICIAL BLADDER

FIELD OF INVENTION

This invention relates to an implantable artificial bladder for the collection of, the storage of, and discharge of biological fluids, more particularly urine, in a patient whose natural bladder failed or has been removed.

BACKGROUND OF INVENTION

The estimated incidence of bladder carcinoma in the United States in 1990 is 49,000. Of these patients, 3,000 will have a cystectomy performed, and many more cystectomies and urinary diversions will be done for disabling functional disorders of the bladder.

At the present time, these patients are provided with conduits, continent pouches or ureterosigmoidostomy. Although these intestinal urinary diversions are markedly better than bilateral ureterostomies, the long list of physical and psychological complications associated with their use has spurred investigation into a total alloplastic replacement of the lower urinary tract. Several set-backs, however, have arisen with the present design of the replacement devices. The three main problem areas that still need to be overcome are renal failure from hydronephrosis, infection from urinary statis and external connections and encrustation of the luminal surface.

Most artificial bladder replacements have relied on ureteric pressure to expand a flexible bladder. Unfortunately, when these bladders are placed intraabdominally, a fibrous capsule has developed around the prosthesis restricting the filling of the bladder. This restriction can cause a retention of urine by the kidneys and the development of hydronephrosis.

In addition, in most prosthesis, gravity has been the basis of bladder emptying. Although this has been effective on bench testing, most models have been found to have large residual volumes of urine after implementation. A fibrous capsule can also cause retention of urine because it inhibits complete collapse of the bladder. The presence of this residual urine increases the risk of encrustation and can lead to infection and stone formation. Therefore, there arises the need for an artificial bladder that overcomes hydronephrosis and reduces the risk of infection and encrustation.

SUMMARY OF INVENTION

The present invention is for an artificial bladder that reduces the risk of hydronephrosis by negative pressure drainage of the kidneys. The invention also reduces the risk of infection and encrustation by active voiding of the bladder system to insure that no residual urine remains in the bladder after emptying.

The invention incorporates a bladder with a hard outer shell and a collapsible inner shell. The outer and inner shell are connected at a bladder neck leaving an open space between the outer shell and the inner shell that is filled with a biocompatible fluid. The hard outer shell of the invention prevents any interference from the surrounding tissues to prevent them from restricting the filling or emptying of the bladder.

The bladder is connected in series with a reservoir that is arranged and configured to create a negative pressure gradient between the reservoir in the bladder and a pumping means to enable the biocompatible fluid to flow between the bladder, reservoir and pump. Ureter tubes are connected to the kidneys and to the bladder neck so that urine can flow from the kidneys to the bladder inner shell. The negative pressure gradient between the reservoir and the bladder causes the biocompatible fluid to flow from the open space in the bladder to the reservoir, which in turn causes urine to be drawn from the kidneys into the bladder inner shell. This negative pressure drainage of the kidneys prevents backflow of urine from the bladder to the kidneys, therefore, preventing renal failure from hydronephrosis.

When the bladder is full, the patient activates the pump causing biocompatible fluid to flow from the reservoir, through the pump and into the open space in the bladder. As the biocompatible fluid is forced into the open space from the pump the bladder inner shell collapses forcing the urine through a valve and out of the body. This active voiding of urine from the bladder assures that no urine remains in the bladder, therefore, reducing the risk of an infection and encrustation.

BRIEF DESCRIPTION OF THE DRAWINGS

FIG. 1 is a front elevational view of the preferred embodiment of the invention;

FIG. 2 is a side elevational view of the preferred embodiment of the invention with portions of the reservoir cut away;

DETAILED DESCRIPTION OF THE PREFERRED EMBODIMENT

Figure 5:
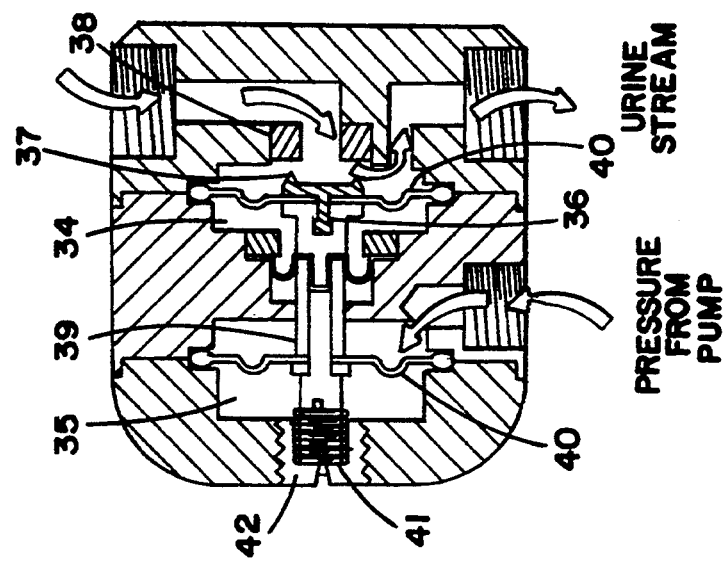
FIG. 5 is an elevational view of the preferred embodiment of the urethral valve in its open position.

Referring to the drawings wherein like numerals designate like parts, the preferred embodiment of the invention is an artificial bladder 10 generally shown in FIG. 1 for implementation into a patient. The artificial bladder 10 is comprised of a bladder generally identified as 11, a reservoir generally identified as 12, a pump 13, a urethral valve 14, a urethra tube 15, ureter tubes 16, a first tubing member 17, a second tubing member 18, a third tubing member 19 and a fourth tubing member 20.

The bladder 11 is comprised of a 300-ml hard outer shell 24 made of rigid polysulphone and a 230-ml flexible inner shell 25 made of silicone. The outer shell 24 and inner shell 25 are connected at the bladder neck 26 creating an open space 27 between the outer shell 24 and inner shell 25. The inner shell 25 is flexible and expands as urine enters the bladder 11. The open space 27 contains saline or some other suitable biocompatible fluid and is separated from the urine stream by the attachment of the inner shell 25 at the bladder neck 26.

In the preferred embodiment, the ureter tubes 16 are made of 8-f silicone tubing reinforced with a nylon spiral to prevent kinking. The proximate end of ureter tube 16 contains a 4.5-f silicone pigtail 21 for insertion into the renal pelvis, and a 0.5-cm. dacron cuff 22 that is used to facilitate anastomosis with the uretic stump. The placement of the pigtail 21 in the renal pelvis overcomes the problem of papilloma formation by reducing irritation and increasing the distance of the connection of the ureter tube 16 from the site of anastomosis.

At the distal end of the ureter tube 16 is a silicone latex rubber duckbill antireflux valve 23. This antireflux valve 23 allows urine to flow through the ureter tube 16 to the inner shell 25 of the bladder 11 during the filling of the bladder 11, but prevents the flow of urine from the inner shell 25 to the ureter tube 16 during the emptying of the bladder 11.

The reservoir 12, best shown in FIG. 2, is comprised of a polysulphone rigid base 28, generally shaped like a truncated cone, and a flexible silicone dome 29, which are compressed together by two stainless steel rings 30 to form a fluid tight chamber. An 11-cm. stainless steel spring 31 is located inside the reservoir 12 with one end attached to the rigid base 28 and the other end attached to the flexible dome 29. This reservoir 12 arrangement is used to create a negative pressure gradient as compared to the secretory pressure of the kidney which is believed to be between 2 and 10 cm of $H_2O$.

The pump 13 is preferably of a manual operation design and is placed on the inside of the patient near the skin in a location that is easily accessible by the patient. One such location could be the scrotum. The pump 13 used in this preferred embodiment is made of silicone and is unidirectional having a 2-ml volume. Those skilled in the art would recognize that electrical or electromechanical pumps could also be used.

One end of an 8-f first tubing member 17 is attached to an aperture in the outer shell 24 of the bladder 11 and the opposite end of the first tubing member 17 is attached to an aperture in the reservoir rigid base 28, thereby enabling saline to travel from the bladder 11 to the reservoir 12. The negative pressure gradient between the reservoir 12 and bladder 11 causes saline to flow from the bladder 11 to the reservoir 12. The first tubing member 17, therefore, also contains a polysulphone orifice 32 to regulate the rate of fluid moving from the bladder 11 to the reservoir 12. Four parallel ceramic filters 33 are also contained in the first tubing member 17 and are located between the bladder 11 and the orifice 32 to remove any particulate matter that might obstruct the orifice 32.

One end of a 8-f silicone second tubing member 18 is attached to an aperture in the rigid base 28 of the reservoir 12 and the other end is attached to the pump 13 to allow saline to flow from the reservoir 12 to the pump 13. One end of an 8-f silicone third tubing member 19 is attached to the pump 13 and the other end is attached to an aperture in the outer shell 24 of the bladder 11. The third tubing member 19 also contains an antireflux valve 43 at the attachment to the bladder 11 to allow saline to flow from the pump 13 to the bladder 11, but preventing saline from flowing from the bladder 11 to the pump 13.

Figure 4:
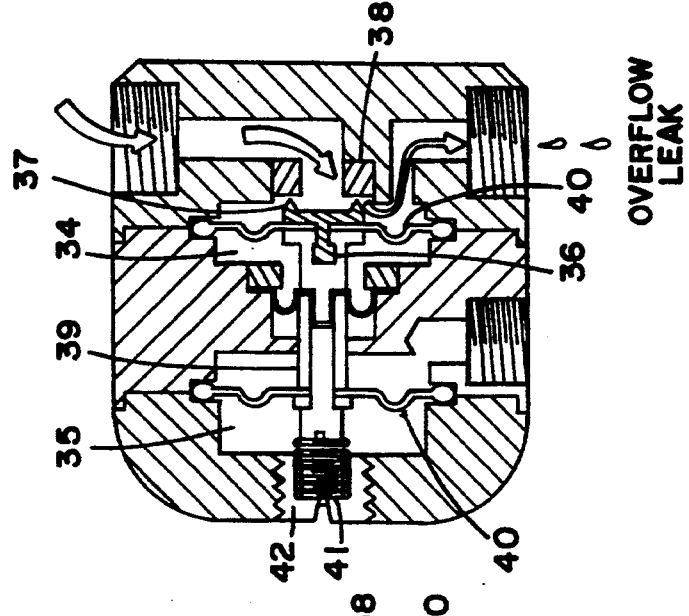
FIG. 4 is an elevational view of the preferred embodiment of the urethral valve as positioned when the bladder is full.
Figure 3:
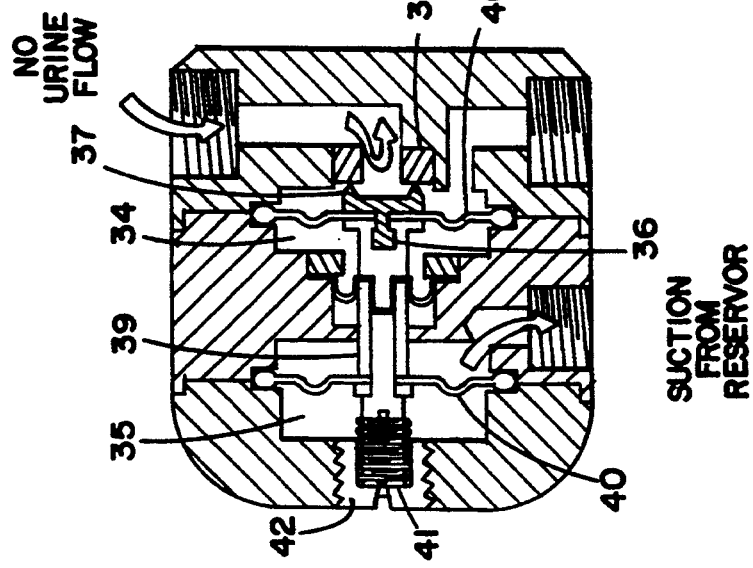
FIG. 3 is an elevational view of the preferred embodiment of the urethral valve in its closed position.

The preferred embodiment of the urethral valve 14, best shown in FIGS. 3–5, is a machined polysulphone valve that is divided into a first chamber 34 and a second chamber 35. The first chamber 34 is connected both to the urethra tube 15 and to the bladder neck 26 and thus acts as the urine conduit. A stainless steel poppit 36 with a sharp rim 37 around its edge is located in the first chamber 34 on one end of a central rod 39. The sharp rim 37 abuts a silicone seat 38 to create a watertight seal that obstructs urine flow when the urethral valve 14 is closed. The central rod 39 extends through both the first chamber 34 and second chamber 35 and is supported by flexible silicone diaphragms 40 which enable the central rod 39 to move back and forth in an axial direction. A valve spring 41 and screw cap 42 are located on the end of the central rod 39 opposite to the poppit 36 to insure that the urethral valve 14 is closed when in the resting position. The screw cap 42 can be adjusted to change the amount of compression in the valve spring 41 to change the opening or leak pressure of the urethral valve 14.

The second chamber 35 is connected to the reservoir 12 and the pump 13 by an 8-f silicone fourth tubing member 20 that has one end attached to the second chamber 35, a second end attached to the first tubing member 17 and a third end attached to the third tubing member 19. The second chamber 35 is thereby placed in fluid connection with the reservoir 12 and the pump 13.

The preferred embodiment of the urethral tube 15 is an 18-f silicone tube with a dacron cuff 44 generally located at its proximal end for attachment to the urethral stump. In the preferred embodiment, the urethra tube 15 extends beyond the sphincter to eliminate the problems with urine leaks at the urethral anastomosis that exist in shorter ureter tube 15 designs.

During bladder filling, the negative pressure in the reservoir 12 causes saline to be drawn from the open space 27 in the bladder 11 through the first tubing member 17 and into the reservoir 12. This removal of saline creates a negative pressure in the inner shell 25 of the bladder 11 causing urine to be drawn from the kidneys, through the ureter tube 16 and into the inner shell 25 of the bladder 11. This negative pressure drainage of the kidneys eliminates the problem of hydronephrosis that can be present with existing designs.

The negative pressure in the reservoir 12 also causes the diaphragm 40 located in the second chamber 35 of the urethral valve 14 to be drawn axially toward the poppit 36 helping to seal the first chamber 34, FIG. 3. As the reservoir 12 continues to fill with saline, the pressure in the reservoir will increase, reducing the negative pressure gradient between the reservoir 12 and the bladder 11. When the inner shell 25 of the bladder 11 is full, the pressure from the urine on the diaphragm 40 in the first chamber 34 will be great enough to cause the poppit 36 to open slightly allowing a small amount of urine to leak through the first chamber 34, FIG. 4. This leakage acts as a signal to the patient that the bladder 11 is full and needs to be emptied.

The patient then activates the pump 13 to empty the bladder 11. As the pump 13 is activated, the pressure of the saline in the second chamber 35 is increased forcing the diaphragm 40 in the second chamber 35 of the urethral valve 14 to move toward the valve spring 41, forcing the central rod 39 to move toward the valve spring 41 and opening the first chamber 34, FIG. 5. The activated pump 13 also draws saline from the reservoir 12 and forces it into the open space 27 increasing the pressure in the bladder 11 and causing the inner shell 25 to collapse. The collapsing of the inner shell 25 assures that the bladder 11 is completely emptied. However, this increased pressure in the bladder 11 requires the use of the antireflux valves 23 on the ureter tubes 16 to prevent urine from backing up into the kidneys.

Figure 6:
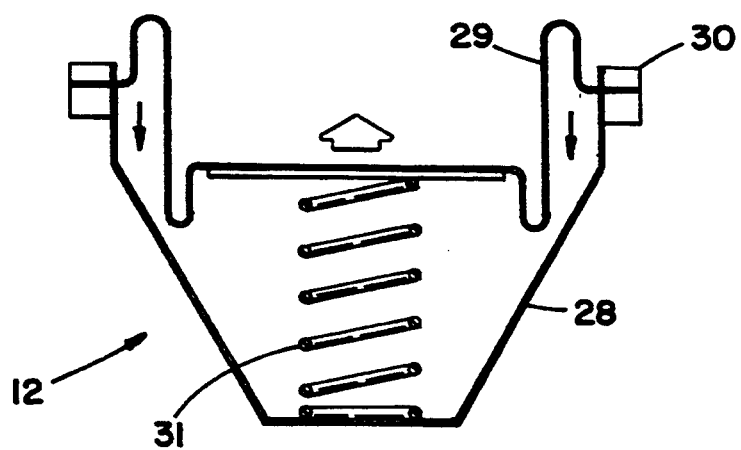
FIG. 6 is a schematic illustration of the reservoir as shown when the reservoir is empty.

In addition, as the pump 13 draws saline from the reservoir 12, the pressure in the reservoir 12 is decreased causing the silicone dome 29 to collapse and the spring 31 to compress, FIG. 6. By the time the patient discontinues the use of the pump 13, the pressure in the reservoir 12 is again lower than the pressure of the bladder 11, causing the saline to be drawn from the bladder 11 to the reservoir 12 and urine to be drawn from the kidneys to the bladder 11. As saline continues to enter the reservoir 12, the pressure in the reservoir 12 will increase, allowing the spring 31 to expand moving the silicone dome 29 outward and thereby increasing the volume of the reservoir 11. The changing volume of the reservoir 12 creates a smooth pressure transition as the reservoir 12 fills with saline and the pressure of the reservoir 12 increases.

Although characteristics and advantages together with details for structure, materials, function and process steps have been described in reference to a preferred embodiment herein, it is understood that the disclosure is illustrative. To that degree, various changes made, especially to the matters of shape, size and arrangement, to the full extent extended by the general meaning of the terms in which the appended claims are expressed, are within the principals of the present invention.

What is claimed is:

1. An implantable artificial bladder for implementation into a patient comprising:

(a) a bladder having a rigid outer shell and an inner flexible shell connected to the rigid outer shell at a bladder neck such that an open space exists between the outer shell and the inner flexible shell;

(b) ureter tubes having a kidney-oriented end, a bladder-oriented end and an anti-reflex valve, wherein the kidney-oriented end is configured to be attached to the patient such that urine can move from a patient's kidney to the ureter tube, the bladder-oriented end is attached to the bladder such that the ureter tube is in fluid communication with the inner flexible shell and the anti-reflex valve is arranged and configured to allow urine to move from the kidneys to the inner flexible shell and to prevent urine from moving from the inner flexible shell to the kidneys;

(c) a reservoir having a rigid base, a flexible dome, and securing means for securing the flexible dome to the rigid base to create a fluid-tight reservoir with a variable volume;

(d) a spring-type member located within the reservoir having base-oriented and dome-oriented ends, wherein the base-oriented end is connected to the rigid base and the dome-oriented end is connected to the flexible dome;

(e) a first tubing member with reservoir-oriented and bladder-oriented ends, wherein the reservoir-oriented end is connected to the reservoir such that the first tubing member is in fluid communication with the reservoir and the bladder-oriented end is connected to the bladder such that the bladder-oriented end is in fluid communication with the open space in the bladder;

(f) an urethral valve having a first chamber with a top and bottom opening, a second chamber, and valve means for allowing or preventing fluid to move from the top opening to the bottom opening of the first chamber, wherein the urethral valve is attached to the neck of the bladder such that the top opening of the first chamber is in fluid communication with the inner flexible shell;

(g) pumping means for pumping biocompatible fluid from the reservoir to the open space in the bladder and from the reservoir to the second chamber of the urethral valve such that the valve means is opened to allow fluid to move from the top opening to the bottom opening of the first chamber when the pumping means is activated;

(h) an urethra tube attached to the bottom opening of the first chamber which is arranged and configured to allow urine to exit the patient;

(i) a second tubing member with reservoir-oriented and pump-oriented ends, wherein the reservoir-oriented end is connected to the reservoir such that the second tubing member is in fluid communication with the reservoir and wherein the pump-oriented end is connected to the pumping means such that the second tubing member is in fluid communication with the pumping means;

(j) a third tubing member with a pump-oriented end, a bladder-oriented end, and an anti-reflux valve, wherein the pump-oriented end is connected to the pumping means such that the third tubing member is in fluid communication with the pumping means, the bladder-oriented end is connected to the bladder such that the third tubing member is in fluid communication with the open space in the bladder and wherein the anti-reflux valve is arranged and configured such that biocompatible fluid can move from the pumping means to the open space in the bladder, but the biocompatible fluid cannot move from the open space in the bladder to the pumping means; and (k) a fourth tubing member with a valve-oriented end, a first-tubing-oriented end, and a third-tubing-oriented end, wherein the valve-oriented end is connected to the second chamber of the urethral valve such that the second chamber is in fluid communication with the fourth tubing member, the first-tubing-oriented end is connected to the first tubing member such that the fourth tubing member and first tubing member are in fluid communication and wherein the third-tubing-oriented end is connected to the third tubing member, such that the third tubing member is in fluid communication with the fourth tubing member.

2. An implantable artificial bladder for implementation into a patient comprising:

(a) a bladder having a rigid outer shell and an inner flexible shell connected to the rigid outer shell at a bladder neck such that an open space exists between the outer shell and the inner flexible shell, the open space containing a biocompatible fluid at a predetermined pressure;

(b) ureter means configured to be attached to the patient and the bladder for allowing urine to move from a patient's kidneys to the inner flexible shell of the bladder;

(c) flow-restricting means attached to the ureter means for preventing urine from moving from the inner flexible shell to the kidneys;

(d) storage means for storing the biocompatible fluid at a pressure lower than the pressure of the biocompatible fluid in the open space;

(e) first connecting means attached to the storage means and the bladder for allowing the biocompatible fluid to move from the open space to the storage means;

(f) valve means for allowing urine to exit or for preventing urine from exiting the inner flexible shell of the bladder;

(g) pumping means for pumping the biocompatible fluid from the storage means to the open space in the bladder;

(h) second connecting means attached to the storage means and pumping means for allowing the biocompatible fluid to move from the storage means to the pumping means;

(i) third connecting means attached to the pumping means and the bladder for allowing the biocompatible fluid to move from the pumping means to the open space in the bladder; and (j) urethra means attached to the valve means for allowing urine to exit the patient from the valve means.

3. An implantable artificial bladder according to claim 2, wherein the ureter means includes a silicone tube reinforced with a nylon spiral to prevent kinking.

4. An inplantable artificial bladder according to claim 2, wherein the flow-restricting means includes an anti-reflux valve attached to the ureter means.

5. An implantable artificial bladder according to claim 2, wherein the first connecting means includes a silicone tube having an orifice for limiting the movement of biocompatible fluid from the open space in the bladder to the storage means.

6. An implantable artificial bladder according to claim 2, wherein the pumping means includes a manually-operated silicone pump configured to be implanted inside the patient and located near the patient's skin.

7. An implantable artificial bladder according to claim 2, wherein said valve means includes a urethral valve having a first chamber with a top and bottom opening, a second chamber, a spring-loaded poppet and a fourth connecting means attached to the first connecting means, the third connecting means and the urethral valve such that the second chamber is in fluid communication with the first connecting means and third connecting means, the urethral valve being attached to the bladder neck such that the top opening is in fluid communication with the inner flexible shell and the bottom opening being attached to the ureter means such that the bottom opening is in fluid communication with the ureter means and wherein the spring-loaded poppet is biased to provide a fluid-tight seal in the first chamber between the top opening and bottom opening, but opens upon activation of the pumping means.

8. An implantable artificial bladder according to claim 2, wherein the storage means includes a reservoir having a rigid base, a flexible dome, securing means for securing the flexible dome to the rigid base to create a fluid-tight reservoir with a variable volume, and a spring-type member located within the resrevior having base-oriented and dome-oriented ends wherein the base-oriented end is connected to the rigid base and the dome-oriented end is connected to the flexible dome.

9. An implantable artificial bladder according to claim 8, wherein the securing means includes a plurality of rings which compress the flexible dome to the rigid base.

10. An implantable artificial bladder according to claim 2, wherein the second connecting means includes a silicone tube.

11. An implantable artificial bladder according to claim 2, wherein the second connecting means includes a silicone tube having an anti-reflex valve which is arranged and configured to allow biocompatible fluid to move from the pumping means to the open space, but to prevent biocompatible fluid from moving from the open space to the pumping means.

12. An implantable artificial bladder according to claim 2, wherein the ureter means includes a silicone tube which is connected to the valve means and the patient's ureter.

* * * * *